United States Patent [19]
Smith et al.

[11] Patent Number: 4,786,493
[45] Date of Patent: Nov. 22, 1988

[54] HAIR PROTECTION COMPOSITION

[75] Inventors: Walter P. Smith, Head-Of-The-Harbor; Frederick J. Penna, Ronkonkoma, both of N.Y.

[73] Assignee: Estee Lauder Inc., New York, N.Y.

[21] Appl. No.: 800,999

[22] Filed: Nov. 22, 1985

[51] Int. Cl.$^4$ .................. A61K 7/06; A61K 7/42; A61K 7/44; A61K 9/12

[52] U.S. Cl. .................. 424/59; 424/47; 424/60; 424/70; 514/944

[58] Field of Search .................. 424/70, 59, 60

[56] References Cited

U.S. PATENT DOCUMENTS

| | | | |
|---|---|---|---|
| 2,250,553 | 7/1941 | Ruskin | 424/14 |
| 2,283,817 | 5/1942 | Martin et al. | 424/106 |
| 2,577,710 | 12/1951 | McDonough | 424/72 |
| 2,780,579 | 2/1957 | Schwartz et al. | 424/71 |
| 3,145,146 | 8/1964 | Liebermen et al. | 424/32 |
| 3,160,564 | 12/1964 | Hanus | 424/95 |
| 3,215,685 | 11/1965 | Nakanishi et al. | 536/118 |
| 3,218,234 | 11/1965 | Wilmsmann et al. | 424/70 |
| 3,230,228 | 1/1966 | Erlemenn et al. | 260/295 |
| 3,285,818 | 11/1966 | Ohta et al. | 424/70 |
| 3,335,054 | 8/1967 | Reynolds et al. | 424/59 |
| 3,671,643 | 6/1972 | Kalopissis | 424/330 |
| 3,694,141 | 9/1972 | Kalopissis et al. | 424/70 |
| 3,790,664 | 2/1974 | Krochock et al. | 424/47 |
| 3,849,576 | 11/1974 | Kalopissis | 424/70 |
| 3,898,243 | 8/1975 | Mecca | 424/68 |
| 3,950,542 | 4/1976 | Kalopissis et al. | 424/DIG. 4 |
| 3,954,989 | 5/1976 | Mecca | 424/68 |
| 4,129,644 | 12/1978 | Kalopissis et al. | |
| 4,169,139 | 9/1979 | Karler et al. | 424/106 |
| 4,203,997 | 5/1980 | Küppers et al. | 424/14 |
| 4,283,386 | 8/1981 | Van Scott et al. | 424/70 |
| 4,294,852 | 10/1981 | Wildnauer et al. | 424/150 |
| 4,436,722 | 3/1984 | Matsunaga et al. | 424/70 |
| 4,478,853 | 10/1984 | Chaussee | 424/73 |
| 4,504,644 | 3/1985 | Lang et al. | 527/201 |
| 4,515,778 | 5/1985 | Kastell | 424/95 |
| 4,520,012 | 5/1985 | Alfonsi | 424/95 |

FOREIGN PATENT DOCUMENTS

62649 7/1968 German Democratic Rep. ... 424/70

OTHER PUBLICATIONS

J. McCord, *Science*, 185, 529–531 (1974).
B. M. Babior et al., *J. Clin. Invest.*, 52, 741–744 (1973).
I. Fridovich, *J. Biol. Chem.*, 245, 4053–4057 (1970).
P. C. Jocelyn, *Biochem. J.*, 117, 951–956 (1970).
M. L. Salin and J. M. McCord, "Free Radicals in Leukocyte Metabolism and Inflammation", in A. M. Michelson et al., Ed., *Superoxide and Superoxide Dismutases*, pp. 257–270, Academic Press, London (1977).
H. M. Hasson and I. Fridovich, "Chemistry and Biochemistry of Superoxide Dismutases", *European Journal of Rheumatology and Inflammation*, 4, 160–172 (1981).
Chemical Abstract 93:210109p (1980), corresponding to Japan Kokai, Tokkyo Koho 80 87,712.
Chemical Abstract 89:152577u, corresponding to Japan Kokai 78 75,340.

*Primary Examiner*—Dale R. Ore
*Attorney, Agent, or Firm*—Richard M. Barnes

[57] ABSTRACT

Disclosed are a composition for protecting hair from damage caused by exposure to ultraviolet light and a method of using the composition. The composition comprises:

(a) a first component selected from the group consisting of a material having superoxide dismutase activity, ascorbic acid, Cytochrome C, mixtures of nicotinamide dehydrogenase and lactate dehydrogenase, uric acid, uric acid salts, and mixtures thereof;

(b) a second component selected from the group consisting of mannitol, catalase, and mixtures thereof, and (c) a third component selected from the group consisting of a disulfide, a thiol, and mixtures thereof, said disulfide and said thiol each having a molecular weight of at least about 100.

20 Claims, No Drawings

HAIR PROTECTION COMPOSITION

FIELD OF THE INVENTION

The present invention relates to a composition for protecting hair from damage caused by exposure to ultraviolet light and to a method of protecting hair from such damage comprising applying an effective amount of the composition to the hair.

BACKGROUND OF THE INVENTION

Hair predominantly comprises certain polypeptide chains that are held together by disulfide bonds that link adjacent polypeptide chains. These bonds, which are formed from two cysteine amino acid residues on the adjacent keratin polypeptides, impart to the hair its mechanical strength and extensibility. Exposure to the sun tends to cause breakage of these disulfide bonds predominantly on the outer surface of the hair, including the outer surface of the hair cuticle. This results in stiffness and brittleness of the hair in dry weather and in frizziness of the hair in humid weather. It also results in the hair losing its color and luster. In addition, the breakage of the disulfide bonds of the keratin causes a protective layer of the hair to be broken down, thereby resulting in important constituents of the hair being extracted from the hair during washing.

Sun damage to hair has been controlled by utilizing sunscreens which, when deposited on the hair, absorb ultraviolet light that would otherwise be absorbed by the hair itself. Sunscreen containing compositions, however, tend to be very oily, with the result that they typically are not esthetically appealing. Moreover, many commercially available sunscreens are not effective to shield the hair from all the ultraviolet light in sunlight. For example, a formulation of paraaminobenzoic acid (PABA), when it is deposited on the hair, typically might absorb only about 45 percent of the incident UVB ultraviolet radiation and virtually none of the radiation in the UVA region.

SUMMARY OF THE INVENTION

The present invention is directed to a composition for protecting hair from damage caused by ultraviolet light and to a method of protecting hair from such ultraviolet light by applying the composition to the hair. The composition comprises:

(a) a first component selected from the group consisting of a material having superoxide dismutase activity (e.g., a liver glycogen extract or superoxide dismutase itself), ascorbic acid, Cytochrome C, mixtures of nicotinamide dehydrogenase (NADH) and lactate dehydrogenase (LDH), uric acid, uric acid salts (e.g., an alkali metal, alkaline earth metal, or ammonium salt of uric acid), and mixtures thereof;

(b) a second component selected from the group consisting of mannitol, catalase, and mixtures thereof; and (c) a third component selected from the group consisting of a disulfide, a thiol, and mixtures thereof, said disulfide and said thiol each having a molecular weight of at least about 100.

The disulfide and thiol used in our invention preferably have a molecular weight between about 100 and about 1500. We believe that in use, the disulfide or thiol or mixture thereof is absorbed into the hair, where it absorbs ultraviolet light that would otherwise be absorbed by the cysteine residues of the keratin in the hair.

We also believe that the disulfide or thiol or mixture thereof reacts with superoxide anions and singlet oxygen that are formed in the hair as a result of the hair's absorption of ultraviolet light. If such a reaction did not occur, the superoxide anions and singlet oxygen might otherwise oxidize cysteine residues of the keratin in the hair.

The first component if the composition of our invention preferably comprises a material selected from the group consisting of a material having superoxide dismutase activity, ascorbic acid, and Cytochrome C. Most preferably, a material having superoxide dismutase activity or mixtures of a material having superoxide dismutase activity and one or more of the other materials listed in paragraph (a) above is used as the first component of our invention. When mixtures of NADH and LDH are used as our first component, preferably the mixture comprises about equal parts by weight of each component.

The second component of our composition is preferably mannitol.

With respect to the third component of our composition, preferred materials are selected from the group consisting of cysteamine, pantethine, pantethine palmitate, thioctoic acid, oxidized glutathione (also referred to as N,N-{dithiobis [1-[(carboxymethyl)carbamoyl]ethylene]}, diglutamine, or glutathione disulfide) and mixtures thereof. Most preferably, the third component comprises pantethine or cysteamine or mixtures thereof.

Four particularly preferred compositions of the present invention comprise:

(1) a material having superoxide dismutase activity (most preferably, superoxide dismutase), mannitol, and cysteamine;

(2) a material having superoxide dismutase activity (most preferably, superoxide dismutase), mannitol and pantethine;

(3) ascorbic acid, mannitol, and pantethine; and (4) ascorbic acid, mannitol, and cysteamine.

The three components of the composition of our invention referred to above are preferably applied to the hair in the form of a mixture with other constituents for treating the hair. For example, the composition of the invention may be in the form of a shampoo, a hair conditioner or a hair grooming aid. The three components comprising our invention preferably constitute about 0.1 to about 10% by weight of the composition that is applied to the hair, the remainder comprising a carrier (which may include fragrance), active ingredients for treating the hair or both.

The composition of the present invention diminishes, to a substantial extent, damage to the hair caused by ultraviolet light. The composition of the present invention also reverses, to at least some extent, damage to the hair that may have already been caused by ultraviolet light.

DETAILED DESCRIPTION OF THE INVENTION

Generally, the ingredients used in the composition of this invention should be suitable for cosmetic use and should be compatible when used together in a particular composition.

A number of commercially available materials having superoxide dismutase activity may be used in the present invention. Superoxide dismutase having an activity of 3000 units per mg of protein is available from Sigma Chemical Company. Another suitable material is Glycogen LR, a liver glycogen extract having a superoxide dismutase activity equal to or greater than 5000 units per mg of protein that is marketed by CenterChem, Inc. Superoxide dismutase products are also marketed by Secol Inc.

One alternative to superoxide dismutase as the first component of orr invention is Cytochrome C. Cytochrome C (greater than 90% purity by weight) is available from Sigma Chemical Company.

With respect to the second component of our invention, catalase (activity greater than 2000 units per mg of protein) and mannitol are available from Sigma Chemical Company.

A number of commercially available materials may be used as the third component of our composition. In particular, cysteamine, pantethine, thioctoic acid and oxidized glutathione are available from Sigma Chemical Company and panthethine palmitate is available from Daiichi Pure Chemical Company.

Preferred compositions of the present invention comprise about 0.1 to about 10 parts by weight of the first component, about 0.02 to about 1 part by weight of the second component, about 0.01 to about 1 part by weight of the third component, and from 0 to about 99.87 parts by weight of a cosmetically acceptable carrier.

In particularly preferred embodiments, the composition of the present invention comprises about 0.5 to about 10 parts by weight of the first component, about 0.1 to about 1 part by weight of the second component, about 0.05 to about 1 part by weight of the third component, and up to about 98.3 parts by weight of a cosmetically acceptable carrier.

The compositions of the present invention may be applied to the hair once a day, or more or less often than once a day. Factors such as length of time spent outdoors, season of the year, condition of the hair, etc., will determine how frequently the compositions of the present invention most desirably are applied to the hair.

The following non-limiting Examples illustrate various compositions of the present invention.

EXAMPLES

Example 1

| SHAMPOO | Parts By Weight |
| --- | --- |
| Water | 52.5 |
| Ammonium Lauryl Sulfate | 40.0 |
| Cocamide DEA | 3.0 |
| Glycogen LR | 0.5 |
| Mannitol | 3.0 |
| Cysteamine | 1.0 |

The above ingredients were mixed together at 60° C. and the pH was adjusted to 5.5 with NaOH and HCl. Mixing was continued until a uniform thickness was obtained.

Example 2

| HAIR CONDITIONER EMULSION | Parts By Weight |
| --- | --- |
| Phase A | |
| Glyceryl stearate | 5.0 |
| Mineral oil | 4.0 |
| Quaternium-33 | 3.0 |

-continued

| HAIR CONDITIONER EMULSION | Parts By Weight |
| --- | --- |
| (Lanoquat 50 from Emery Industries, Inc.) | |
| Polyethylene glycol 30-Castor Oil (Croda, Inc.) | 2.5 |
| Stearamidopropyl dimethylamine lactate | 2.5 |
| Isopropyl myristate | 1.5 |
| Cetearyl palmitate | 0.8 |
| Phase B | |
| Hydrolyzed animal protein | 1.8 |
| Glycogen LR | 0.5 |
| Mannitol | 2.0 |
| Pantethine | 1.0 |
| Magnesium aluminum silicate | 1.0 |
| Deionized Water | 74.2 |
| Phenoxyethanol (preservative) | 0.7 |

Phase A was prepared by mixing its components together and then heating the mixture at 75° until all the mixture was a liquid. Phase B was prepared by mixing its components together. Phase B was then added to Phase A and mixed at about 60° C. Mixing was continued until satisfactory emulsification was achieved.

Example 3

| HAIR STYLING GEL | Parts By Weight |
| --- | --- |
| Carbopol 940 | 0.2 |
| Glycogen LR | 0.5 |
| Mannitol | 3.0 |
| Pantethine | 0.1 |
| Cysteamine | 1.0 |
| Water | 96.2 |

The Carbopol 940 (a thickening agent supplied by B. F. Goodrich Co.) was dissolved in the water, with mixing. The other ingredients were then added. The pH of the mixture was monitored while adding NaOH dropwise until a pH of 7.0 was reached. Mixing was continued until the gel was homogeneous.

Example 4

| HAIR CONDITIONER | Parts By Weight |
| --- | --- |
| Stearyl dimethyl benzyl ammonium chloride | 2.0 |
| (20% by weight solution in water) | |
| Polyquaternium 11 | 2.0 |
| (20% by weight solution in water) | |
| (G.A.F., Inc.) | |
| Isostearyl alcohol | 1.0 |
| Fragrance | 0.3 |
| SDA-40 Alcohol (denatured ethanol) | 40.0 |
| (Steppan Chemical Company) | |
| Water | 49.1 |
| Isoceteth 20 (ICI Americas) | 1.0 |
| Glycogen LR | 0.5 |
| Mannitol | 3.0 |
| Cysteamine HCL | 0.5 |
| Pantethine | 0.5 |
| Simethicone (Dow Corning, Inc.) | 0.1 |

The stearyl dimethyl benzyl ammonium chloride, polyquaternium 11, isostearyl alcohol, and fragrance were added to the SDA-40 alcohol, with mixing, until the mixture was homogeneous, to form mixture A.

The isoceteth 20 was melted at 50° C. and then added to water, with mixing, to form mixture B. Mixing was continued until the mixture was homogeneous. Mixture B was then added to mixture A.

Glycogen LR, mannitol, cysteamine HCl and pantethine were then added, one at a time, with mixing, to the combination of mixtures A and B. Mixing was continued until the mixture was homogeneous. The simethicone was then added and mixing was continued until the mixture was homogeneous.

The mixture was then used to fill a spray container. The container was then pressurized with isobutane, using 60 parts by weight of isobutane to 40 parts by weight of the aforementioned mixture.

If desired, rather than using a pressurized container, as described in the preceding paragraph, the hair conditioner of this Example may be poured from a bottle into the hand and then applied to the hair by hand. Alternatively, it may be applied with a pump spray.

We claim:

1. A composition for protecting hair from damage caused by exposure to ultraviolet light, said composition comprising:
   (a) an effective amount of first component selected from the group consisting of a material having superoxide dismutase activity, ascorbic acid, Cytochrome C, mixtures of nicotinamide dehydrogenase and lactate dehydrogenase, uric acid, uric acid salts, and mixtures therof;
   (b) an effective amount of a second component selected from the group consisting of mannitol, catalase, and mixtures thereof,
   (c) an effective amount of a third component selected from the group consisting of a disulfide, a thiol, and mixtures thereof, said disulfide and said thiol each having a molecular weight of at least about 100; and
   (d) a cosmetically acceptable carrier.

2. The composition of claim 1, wherein the first component is selected from the group consisting of a material having superoxide dismutase activity, ascorbic acid, Cytochrome C, and mixtures thereof.

3. The composition of claim 1, wherein the second component is mannitol.

4. The composition of claim 1, wherein the third component is selected from the group consisting of pantethine, cysteamine, pantethine palmitate, thioctoic acid, oxidized glutathione, and mixtures thereof.

5. The composition of claim 1, wherein the third component is selected from the group consisting of pantethine, cysteamine, and mixtures thereof.

6. The composition of claim 1, comprising about 0.1 to about 10 parts by weight of the first component, about 0.02 to about 1 part by weight of the second component, about 0.01 to about 1 part by weight of the third component, and up to about 99.87 parts by weight of the cosmetically acceptable carrier.

7. The composition of claim 6, wherein the first component is selected from the group consisting of a material having superoxide dismutase activity, ascorbic acid, Cytochrome C, and mixtures thereof, the second component is mannitol, and the third component is selected from the group consisting of pantethine, cysteamine, pantethine palmitate, thioctoic acid, oxidized glutathione, and mixtures thereof.

8. The composition of claim 6 wherein the composition comprises about 0.1 to about 5 parts by weight of the first component.

9. The composition of claim 7, wherein said first component is a material having superoxide dismutase activity and said third component is pantethine.

10. The composition of claim 7, wherein said first component is a material having superoxide dismutase activity and said third component is cysteamine.

11. The composition of claim 7, wherein said first component is ascorbic acid and said third component is pantethine.

12. The composition of claim 7, wherein said first component is ascorbic acid and said third component is cysteamine.

13. A method of protecting hair from damage caused by exposure to ultraviolet light comprising applying to the hair an effective amount of the composition of claim 1.

14. A method of protecting hair from damage caused by exposure to ultraviolet light comprising applying to the hair an effective amount of the composition of claim 6.

15. A method of protecting hair from damage caused by exposure to ultraviolet light comprising applying to the hair an effective amount of the composition of claim 7.

16. A method of protecting hair from damage caused by exposure to ultraviolet light comprising applying to the hair an effective amount of the composition of claim 8.

17. A method of protecting hair from damage caused by exposure to ultraviolet light comprising applying to the hair an effective amount of the composition of claim 9.

18. A method of protecting hair from damage caused by exposure to ultraviolet light comprising applying to the hair an effective amount of the composition of claim 10.

19. A method of protecting hair from damage caused by exposure to ultraviolet light comprising applying to the hair an effective amount of the composition of claim 11.

20. A method of protecting hair from damage caused by exposure to ultraviolet light comprising applying to the hair an effective amount of the composition of claim 12.

* * * * *

UNITED STATES PATENT AND TRADEMARK OFFICE
CERTIFICATE OF CORRECTION

PATENT NO. : 4,786,493
DATED : November 22, 1988
INVENTOR(S) : Walter P. Smith and Frederick J. Penna It is certified that error appears in the above-identified patent and that said Letters Patent is hereby corrected as shown below:

| Column | Line | |
| --- | --- | --- |
| 3 | 8 | Change "orr" to --our-- |

Signed and Sealed this

Twenty-eighth Day of May, 1991

*Attest:*

HARRY F. MANBECK, JR.

*Attesting Officer*     *Commissioner of Patents and Trademarks*